United States Patent [19]

Peetermans et al.

[11] 3,962,423
[45] June 8, 1976

[54] LIVE INFLUENZA TYPE B VIRUS VACCINES AND PREPARATION THEREOF

[75] Inventors: Julien Peetermans, Rixensart; Michèle Lobmann, Ceroux-Mousty; Jean-Marie Prevost; Emil Vascoboinic, both of Brussels, all of Belgium

[73] Assignee: Recherche et Industrie Therapeutiques (R.I.T.), Belgium

[22] Filed: Apr. 18, 1975

[21] Appl. No.: 569,258

Related U.S. Application Data

[63] Continuation-in-part of Ser. No. 439,176, Feb. 4, 1974, abandoned.

[52] U.S. Cl. ............................. 424/89; 195/1.1; 195/1.3
[51] Int. Cl.² ................................. A61K 39/18
[58] Field of Search .................. 424/89; 195/1.1–1.8

[56] References Cited
OTHER PUBLICATIONS

Peetermans, J. et al., Dev. Biol. Stand., vol. 28: 340–346 (1975) "Immune Response to Combined Live Influenza Virus Vaccines Administered Intranasally."

Kilbourne, E. D. et al., J. Infect. Dis. 124(5): 449–462 (1971) "Correlated Studies of a Recombinant Influenza Virus Vaccine I."

Schulman, J. L. et al., J. Infect. Dis. 124(5): 463–472 (1971) "Correlated Studies of a Recombinant Influenza Virus Vaccine II."

Kilbourne, E. D., Hospital Practice, Oct. 1971, "Influenza: The Vaccines" pp. 103–114.

Fazekas de St. Groth, S. Bull. Wld. Hlth. Org. 41: 651–657 (1969) "New Criteria for the Selection of Influenza Vaccine Strains".

*Primary Examiner*—Shep K. Rose
*Attorney, Agent, or Firm*—Alan D. Lourie; William H. Edgerton

[57] ABSTRACT

Attenuated stable influenza type B virus strains are obtained by recombining a vaccinal and previously attenuated influenza type B virus strain with an influenza type B virus isolate having the desired serotype and isolating a recombinant having at least one marker property of the attenuated parent strain which is not shared by the other parent strain and the antigenic composition of the other parent strain. The obtained strains are useful for the production of nasal influenza vaccines.

12 Claims, No Drawings

LIVE INFLUENZA TYPE B VIRUS VACCINES AND PREPARATION THEREOF

This application is a continuation-in-part of our copending application Ser. No. 439,176 filed Feb. 4, 1974 now abandoned.

This invention relates to live influenza virus vaccines for nasal administration comprising as active ingredient an attenuated stable type B influenza virus strain and, additionally, an attenuated stable type A influenza virus administrable by nasal route, and to a process of preparing said attenuated stable influenza virus vaccines.

Protection against viral respiratory infections has been shown to be related to the presence of a local immunity in the respiratory mucosa. This aspect has been reviewed recently by Rossen et al. (Progr. Med. Virol. 1971, 13, 194).

Several attempts were made in recent years to induce immunity against influenza by the nasal application of inactivated vaccines (see e.g. Waldman et al. Nature, 1968, 218, 594; JAMA 1969, 207, 520; WHO Bull. 1969, 41, 543). The results were inconsistent, however, and this was probably due to the insufficient stimulation of the immunity system by the inactivated antigen (Tyrrell et al. J. Hyg. 1970, 68, 359).

Live influenza type B virus vaccines are known but are presenting widely varying protection rates and numerous efforts have been made e.g. by serial passages on eggs (see for instance A. A. Smorodintsev, Proc. Symposium on Acute respiratory Diseases, Zagreb 1969, 391–404) or by using low temperature mutants (F. M. Davenport et al. Proc. Symposium on Live Influenza Vaccines, Zagreb 1971, 105–113) to reduce pathogenicity of the virus.

Recombination of influenza type B virus strains is also mentioned in the literature (see for instance E. D. Kilbourne in Progr. Med. Virol. 5, 79–126, 1963).

As indicated for instance by G. C. Schild et al. in Brit. Med. J. 4, 127–31, 1973, antigenic variations in its surface antigens is one of the most important characteristics of the influenza virus and a property which produces many problems for the control of influenza by vaccination.

The present invention provides attenuated stable influenza type B virus strains valuable for vaccinal use or production by a process which comprises attenuating a virulent influenza type B virus strain up to getting an attenuated and vaccinal influenza type B virus strain, recombining said attenuated and vaccinal strain with an influenza type B virus isolate and isolating by selective pressure a recombinant having at least one marker property of the attenuated parent strain which is not shared by the other parent strain and the antigenic composition of the other parent strain.

More particularly, the influenza type B attenuated and vaccinal strain is a strain herein referred to as the Brigit strain (deposited in the American Type Culture Collection, 12301 Parklawn Drive, Rockville Md. 20852 under the deposit number ATCC VR786) and which has been obtained by passaging the influenza B/Russia/69 strain (ATCC VR790) in the allantoic cavity of embryonated chicken eggs in the presence of pig serum up to isolating therefrom an attenuated and vaccinal influenza type B virus strain which:

is completely resistant to serum inhibitors
has a positive AOS (allantoic on shell) marker (titration on "allantoic membrane on shell" is described by S. Fazekas de St. Groth and D. O. White in J. Hyg. 56: 151–62, 1958)
is antigenic with no side-effects on ferrets
shows positive hemagglutinin thermosensitivity at 60° C
shows unstable hemagglutination of sheep red blood cells at 30° C.

In the hereinabove process, the recombination step is carried out in any substrate known to the art for accepting growth of influenza type B virus, e.g. embryonated chicken eggs material or foetal bovine kidney tissue culture, more particularly the allantoic cavity of embryonated chicken eggs. The recombination can be performed with any desired type B virus isolate, more particularly a new isolate such as the B/Hong Kong/5/72 (ATCC VR791) or B/Hong Kong/8/73 (ATCC VR792) isolate.

Obviously, the so-obtained recombinant strains may be cloned or submitted to several dilution passages without modifying the essence of the invention.

Recombinants obtained according to this invention from the Brigit strain (ATCC VR786) with either the B/HK/5/72 (ATCC VR791) or the B/HK/8/73 (ATCC VR792) isolate have been assigned the influenza type B virus R 22 strain (ATCC VR788), R 5 strain (ATCC VR787) and R 75 strain (ATCC VR789) designations respectively.

The virus recombinants obtained by the process of this invention are non-pathogenic, immunogenic and valuable for influenza type B live virus vaccine production, using therefore any technique known to the art for live influenza virus vaccine production and/or stabilization. Consequently, the present invention also relates to attenuated influenza type B virus vaccines containing at least one said influenza type B recombinant and to the process of preparing said vaccines therefrom.

According to this embodiment, the invention relates to a method of preparing an attenuated influenza virus vaccine comprising allowing an influenza type B virus strain as obtained by the hereinabove described process to grow in the allantoic cavity of embryonated chicken eggs for a period of time sufficient to permit growth of a large amount of said virus, and harvesting the resulting virus material.

The so-obtained attenuated influenza virus vaccines are administered topically in the nasopharynx at an effective dosage unit (i.e. at least $10^7 EID_{50}$ of virus), said administration being eventually repeated if and when necessary.

For vaccinal use, the virus is preferably kept in freeze-dried form and the vaccine is extemporaneously reconstituted by addition of either water or any other pharmaceutical diluent or composition known to the art for the preparation of nasal preparations such as drops or spray. The vaccine formula may obviously include a stabilizer such as for instance peptone, sucrose and other ones known to the art.

According to another embodiment of the present invention the influenza type B virus strain obtained by the hereinabove described process can be combined with attenuated influenza type A virus vaccines administrable by nasal route.

The present invention thus relates to a process for preparing a live influenza virus vaccine for nasal administration the active ingredient of which comprises at least an effective amount of an attenuated influenza type B virus strain recombinant, which comprises recombining in a substrate known to the art for accepting growth of influenza type B virus —e.g. embryonated chicken eggs or foetal bovine kidney tissue culture and preferably the allantoic cavity of embryonated chicken eggs— an attenuated and vaccinal strain of influenza type B virus —e.g. influenza type B virus Brigit strain (ATCC VR786)— with an influenza type B virus isolate —e.g. the B/HK/5/72 (ATCC VR791) or the B/HK/8/73 (ATCC VR792) isolate— isolating by selective pressure a recombinant —e.g. the influenza type B virus R 22 strain (ATCC VR788) or R 75 strain (ATCC VR789) or R 5 strain (ATCC VR787)— having at least one marker property of the attenuated parent strain which is not shared by the other parent strain and the antigenic composition of the other parent strain, allowing said recombinant to grow in the allantoic cavity of embryonated chicken eggs and, if desired, adding thereto a stabilizer —e.g. peptone or sucrose— and freeze-drying the mixture.

As indicated hereinabove, the present invention also relates to a process for preparing a combination flu vaccine for nasal administration which comprises combining an influenza type B virus vaccine of this invention with an attenuated influenza type A virus vaccine effective on nasal administration —e.g. influenza type A virus Alice strain (ATCC VR776)— as well as the resulting combined vaccines.

The following examples illustrate the present invention; they should not be construed as limiting its scope.

EXAMPLE 1

A sample of the influenza B/Russia/69 strain (ATCC VR790) is submitted to 3 terminal dilution passages on specific pathogen free eggs, for purification. A sample of the last passage is used as seed for the preparation of an experimental lot which is found to be free of avian pathogenic agents and sensitive to serum inhibitors and which shows residual pathogenicity for human beings. Different dilutions (i.e. $10^{-1}$, $10^{-3}$, $10^{-5}$ and $10^{-7}$) of the seed viral material in normal saline are mixed with different concentration of sterile normal pig serum (undiluted, 25 % and 5 %) previously maintained for 15 minutes in a boiling water bath, homogenized and centrifuged at 2,000 rpm for 30 minutes. The supernatant is used for the further step which consists in incubating the virus/serum mixtures at 37° C for 1 hour before inoculating 0.2 ml. aliquots of said mixture into the allantoic cavity of embryonated chicken eggs previously incubated for 8 to 11 days at 37° C and candled (only the surviving eggs are inoculated).

The eggs are then further incubated for a period of time varying between 24 and 96 hours.

At the end of this incubation period, the eggs are candled and the surviving eggs are chilled at 4° C. The allantoic fluid of each series of surviving eggs is harvested separately and tested for the presence of influenza virus by the hemagglutination method. The harvested virus produced by the inoculum of the highest virus dilution in the presence of the highest serum concentration which shows hemagglutination activity (i.e. virus dilution $10^{-6}$ and serum concentration of 25 %) is used for a second passage performed in the same operative conditions.

A total of 5 passages are performed as described hereinabove.

The virus, harvested after 5 passages, produced by the inoculum of the highest virus dilution (i.e. $10^{-6}$) in the presence of the undiluted serum, shows hemagglutination activity and is resistant to serum inhibitors.

Three further passages at terminal dilution are carried out in the absence of serum to clone the obtained resistant mutant and to check the stability of the resistant character. The virus harvested at each of these 3 passages is resistant against the inhibitors of normal serum. The virus at the last passage level, named "Brigit" and deposited at the ATCC under the deposit number VR786, is used as inoculum for the production of a virus seed lot. Therefore, the harvested allantoic fluids are collected and pooled, sterility and safety tested, mixed with peptone to reach a final concentration of 5 % of peptone. A volume of 0.5 ml. of the viral suspension is distributed into 3 ml. vials and freeze-dried to yield the Brigit strain (ATCC VR786) lot.

IN VITRO AND IN VIVO CHARACTERISTICS OF THE MODIFIED VIRUS (Brigit strain)

1. Inhibitor resistance

For testing the resistance against the inhibitors present in normal heated animal serum (previously heated at 75° C for 1 hour), serial twofold dilutions of the heated serums were mixed with four hemagglutinating units of the parent strain and the modified virus. After incubation of one hour at room temperature, chicken red blood cells were added and the results recorded. The results show a complete resistance for the seed lot and for experimental lots produced from this seed lot. In the present specification, this character is recorded as "positive".

2. Antigenicity and absence of side effects

A group of 2 ferrets was inoculated nasally with $10^7-10^8$ $EID_{50}$ of the Brigit strain (ATCC VR786). The temperature of the animals was recorded daily during 8 days p.i. No significant temperature rise was recorded (maximum temperature 39.6° C). A second group of two ferrets was inoculated nasally with $10^7-10^8$ $EID_{50}$ of the B/Russia/69 parent strain (ATCC VR790). Two days after the inoculation the animals showed temperatures of 40.2° C. Hemagglutination-inhibition tests demonstrated that the modified strain induced an antigenic response in ferrets : 14 days after the nasal inoculation, serum antibody titers were very high among the inoculated animals (titer : 1/256) opposed to the uninoculated control group (titer : <1/8).

3. Ratio $EID_{50}/(AOS)ID_{50}$ (AOS marker)

The same inoculum is titrated on embryonated eggs and on the "allantoic membrane on shell" system (titration on allantoic membrane on shell is described by S. Fazekas de St. Groth and D. O. White in J. Hyg. 56, 151-62, 1958). The $EID_{50}/(AOS)ID_{50}$ ratio for the Brigit strain (ATCC VR786) was found $\leq 10^{2.5}$. In the present specification, a ratio $\leq 10^{2.5}$ is indicated as "positive".

4. Hemagglutinin thermosensitivity

Hemagglutination test was performed on infective allantoic fluid incubated for 1 hour at 60° C. After such treatment, Brigit strain (ATCC VR786) has completely lost its hemagglutinating property. This thermosensitivity is herein recorded as positive.

5. Hemagglutination test with sheep red blood cells at 30° C

An hemagglutination test was performed with sheep red blood cells at 4° and 30° C. The hemagglutination pattern at 4° C was normal whereas at 30° C there was a rapid elution so that no clear cut hemagglutination was observed. When examined 20 hrs. after initiation of the test, the hemagglutination has completely disappeared. This character is herein referred to as "unstable".

recombinant virus and the harvested allantoic fluid is supplemented with peptone up to a final concentration of 5 % and freeze-dried.

TABLE I

| Strain | Serotype Brigit | Serotype B/HK 5/72 | inhibitor resistance | $EID_{50}/$ $(AOS) ID_{50}$ | hemagglutinin thermosensitivity | 30°C sheep red blood cells hemagglutination |
|---|---|---|---|---|---|---|
| Brigit | + | − | + | + | + | unstable |
| B/HK/5/72 | − | + | − | − | − | stable |
| Recombinant R 22 (ATCC VR 788) | − | + | + | + | − | stable |

EXAMPLE 2

A sample of influenza type B virus strain B/HK/5/72 (ATCC VR791) the hemagglutinin of which is different from that of the Brigit strain (ATCC VR786), is inoculated in the allantoic cavity of 10 to 11 day-old embryonated eggs (inoculum : 0.2 ml./egg), and submitted to three passages, in order to obtain a substantial amount of virus. At the end of the third passage, a viral suspension is obtained, the titer of which is $10^8 EID_{50}/ml$. Aliquots (0.2 ml.) of the undiluted suspension are inoculated in the allantoic cavity of SPF (specific pathogen free) embryonated eggs; after incubation for 2 hrs. at 33° C, aliquots (0.2 ml.) of a suspension of Brigit strain (ATCC VR786), having a titer of $10^{7.5} EID_{50}/ml$., are inoculated in the same eggs. The eggs are then incubated for 16 hrs. at 33° C and the allantoic fluids are harvested.

Aliquots (0.25 ml.) of anti-Brigit strain serotype rabbit serum previously heated for 1 hr. at 56° C, are mixed with the same volume of normal serum. Aliquots (0.25 ml.) of this serum mixture are added to the harvested allantoic fluids. This mixture is then maintained for 1 hr. at 37° C. Embryonated eggs are inoculated with 0.2 ml. of the incubated mixture (2 eggs for each mixture) and incubated for 48 hrs. at 33° C. The allantoic fluids of each inoculated egg are harvested, passaged in embryonated eggs (0.2 ml. per egg) and incubated for 72 hrs. at 33° C, using two eggs for each sample. After the 72 hrs. incubation period, the positive allantoic fluids are harvested and checked for:
  hemagglutination of sheep red blood cells
  serotype against anti-Brigit serum and against anti-B/HK/5/72 serum
  resistance to non-specific serum inhibitors
  growth in eggs and on AOS (allantoic on shell).
One of the so-obtained viral suspensions which, as indicated in the following Table I, has the serotype of one parent (B/HK/5/72) and the infectivity pattern in the AOS system and the serum inhibitor marker of Brigit strain is assigned the "R 22" designation (ATCC VR788) and submitted to 2 passages on embryonated chicken eggs to obtain a substantial amount of R 22

EXAMPLE 3

Equal volumes of a suspension of the influenza type B Brigit strain (ATCC VR786) and of the B/Hong Kong/8/73 strain (ATCC VR792) (the titer of each being $10^{7.5} EID_{50}/ml$.) are mixed and preincubated for 72 hrs. at 4° C. The mixture is then inoculated in the allantoic cavity of two SPF embryonated eggs (0.2 ml. per egg). After an incubation period of 16 hrs. at 33° C, the allantoic fluids are harvested and sonicated (30 sec.).

The harvested fluids undiluted and diluted to $10^{-1}$ and $10^{-2}$ are allowed to react for 1 hr. at 37° C with different dilutions of anti-Brigit strain serotype rabbit serum previously heated at 56° C for 30 min. The resulting mixtures are inoculated on allantoic on shell system and incubated for 72 hrs. at 37° C. The samples of the last positive virus dilution ($10^{-2}$) are numbered 1 to 7.

Infectivity titers and neutralization by anti-Brigit serum in the AOS system are then compared for the 7 samples and for the two parental strains.

The samples which are not neutralized by anti-Brigit serum and which exhibit an $(AOS)ID_{50}$ titer at least equal to that of Brigit strain (ATCC VR786) are harvested at the highest positive dilution.

These individual harvests are diluted to $10^{-4}$ and passaged once in SPF eggs.

One of these viral suspensions showing the serotype and hemagglutinin thermosensitivity of B/Hong Kong/8/73 strain and the $EID_{50}/(AOS)ID_{50}$ ratio of Brigit strain is assigned the "R 5" designation (ATCC VR787).

In the following Table II the characteristics of recombinant R 5 are summarized and compared to those of the Brigit (ATCC VR786) and B/HK/8/73 (ATCC VR792) parents.

TABLE II

| Strain | Serotype Brigit | Serotype B/HK 8.73 | $EID_{50}/$ $(AOS)ID_{50}$ | hemagglutinin thermosensitivity |
|---|---|---|---|---|
| Brigit | + | − | + | + |
| B/HK/8/73 | − | + | − | − |
| Recombinant R 5 (ATCC VR787) | − | + | + | − |

The R 5 recombinant is submitted to two limit dilution passages (in SPF embryonated chicken eggs) to eliminate any eventual avian adventitious agent and to one further passage to obtain a substantial amount of R 5 recombinant virus. The harvested allantoic fluid is supplemented with peptone up to a final concentration of 5 % and freeze-dried.

EXAMPLE 4

Starting from the freeze-dried materials obtained in Example 1 (i.e. the Brigit strain, ATCC VR786) as seed lot for large scale vaccine production, a further passage is carried out in the allantoic fluid of another set of embryonated chicken eggs with are incubated at 35° C for 3 days.

The allantoic fluids are harvested, pooled, sterility and safety tested, mixed with peptone as stabilizer in order to reach a final concentration of 5 % of peptone and distributed into 3 ml. glass vials in order to obtain a dosage unit (i.e. at least $10^7$ $EID_{50}$) of virus. The product is then freeze-dried and the vials are tightly stoppered.

This passage level is used as vaccine batch. For vaccine administration, the contents of one vial is reconstituted by adding 0.5 ml. of water or saline or a 5 % sucrose solution and administered as drops in the nostrils.

Alternatively, the allantoic fluids peptone preparation is distributed in larger glass vials in order to obtain integers of the dosage unit amount of virus to constitute corresponding multi-doses vaccine preparations.

VACCINATION WITH THE ATTENUATED TYPE B (BRIGIT STRAIN) INFLUENZA VIRUS

Clinical trials were performed in 46 volunteers having a prevaccination HI (hemagglutination inhibition) titer inferior or equal to 32 against influenza B virus. Each volunteer received two intranasal administrations with a 8 or 14 day interval. At each administration, subjects were given a virus concentration of $10^{7.5}EID_{50}$ of Brigit strain (in each nostril 5 drops of the extemporaneously reconstituted vaccine in 5 % sucrose solution in water). Seroconversion was observed in 40 subjects (i.e. 87 %); only mild clinical reactions (i.e. rhinorrhea or stuffy nose for 1 to 2 days) were observed. In the trials were control groups were available, no transmission of influenza vaccine virus was observed. Virus isolation was attempted from nasal and throat swabs but the samples remained negative after two blind passages in embryonated eggs.

EXAMPLE 5

Starting from the freeze-dried R 22 strain (ATCC VR788) obtained in example 2 as seed lot for large scale vaccine production, a further passage is carried out in the allantoic fluid of another set of embryonated chicken eggs which are incubated at 35° C for 3 days.

The allantoic fluids are harvested, pooled, sterility and safety tested, mixed with peptone as stabilizer in order to reach a final concentration of 5 % of peptone and distributed into 3 ml. glass vials in order to obtain a dosage unit (i.e. at least $10^7 EID_{50}$ of virus). The product is freeze-dried and the vials sealed or tightly stoppered.

This passage level is used as vaccine batch. For vaccine administration, the contents of one vial is reconstituted by adding 0.5 ml. of water or saline or a 5 % sucrose solution and administered as drops in the nostrils.

Alternatively, the allantoic fluids/peptone preparation is distributed in larger glass vials in order to obtain integers of the dosage unit amount of virus to constitute corresponding multi-doses vaccine preparations.

VACCINATION WITH THE ATTENUATED TYPE B INFLUENZA VACCINE R 22 STRAIN

Material and methods

Six volunteers having an HI antibody titer inferior or equal to 32 were selected for the trial. Two subjects were taken as control. The 6 subjects received, with a 11 to 14 day interval, two administrations of the extemporaneously reconstituted vaccine, R 22 strain. For each administration, all subjects received 5 drops of the vaccine per nostril ($10^{7.5}EID_{50}$).

Blood samples for antibody determination were taken on vaccination day and on days 10 to 14 after the first inoculation and on day 14 after the second administration. Nasal washings for local antibody determination were taken on day 14 after the second inoculation.

Clinical symptoms

No symptoms were recorded.

Virus isolation.

Nasal swabs were collected on day 3 and 6 in the six subjects. All samples remained negative after two blind passages in embryonated eggs.

Serological results and local antibodies.

Five out of six volunteers developed either a serum or nasal response or both.

The results are summarized in the following Table III.

TABLE III

| Subject | Serum titer (HI) before vaccination | Serum titer (HI) after 2nd vaccination | local antibodies before vaccination (SN) | local antibodies after 2nd vaccination (SN) |
| --- | --- | --- | --- | --- |
| 1 | 32 | 32 | <2 | 24 |
| 2 | 8 | 8 | <2 | 2–4 |
| 3 | 32 | 64 | <2 | 12 |
| 4 | 8 | 32 | <2 | <2 |
| 5 | <8 | <8 | ND | ND |
| 6 | <8 | 16 | ND | ND |

ND = not determined.

EXAMPLE 6

Starting from the freeze-dried material obtained in Example 3 (R 5 strain, ATCC VR787) as seed lot for large scale vaccine production, a further passage is carried out in the allantoic fluid of another set of embryonated chicken eggs which are incubated at 35° C for 3 days.

The allantoic fluids are harvested, pooled, sterility and safety tested, mixed with peptone as stabilizer in order to reach a final concentration of 5 % of peptone and distributed into 3 ml. glass vials in order to obtain a dosage unit (i.e. at least $10^7$ $EID_{50}$) of virus. The mixture is then freeze-dried and the vials sealed or tightly stoppered.

This passage level is used as vaccine batch. For vaccine administration, the contents of one vial is reconstituted by adding 0.5 ml. of water or saline or a 5 % sucrose solution and administered as drops in the nostrils.

Alternatively, the allantoic fluid / peptone preparation is distributed in larger glass vials in order to obtain integers of the dosage unit amount of virus to constitute corresponding multi-doses vaccine preparations.

EXAMPLE 7

To one dosage unit of the freeze-dried influenza type B virus vaccine (Brigit strain,ATCC VR786) prepared as indicated in example 4, there is added one dosage unit of live attenuated type A influenza virus (Alice strain,ATCC VR776) in 0.5ml. of a 5% sucrose solution in water. The so-obtained bivalent vaccine is administered as drops in the nostrils and the administration is repeated 14 days later.

Clinical trials were performed in 22 volunteers having a prevaccination HI (hemagglutination inhibition) titer inferior or equal to 64 against influenza A or B virus. Each volunteer received two nasal administrations ($10^{7.5}$ $EID_{50}$ of the Brigit strain and $10^{7.5}$ $EID_{50}$ of the Alice strain) with a 8 to 14 day interval.

Seroconversion was observed in 80 % of the subjects against influenza type A virus and 73 % against influenza type B virus.

Only mild clinical reactions were observed. No transmission of influenza vaccine virus was observed.

ml. of the mixture and incubated for 48 hrs. at 33° C. The allantoic fluids of each incubated egg are harvested, passaged in SPF embryonated eggs (0.2 ml. per egg) and incubated for 72 hours at 33° C, using two eggs per sample. After the 72 hours incubation period, the positive allantoic fluids are harvested and checked for:

hemagglutination of sheep red blood cells
serotype against anti-Brigit serum and against anti-B/HK/5/72 serum
growth in eggs and on AOS (allantoic on shell)

One of the so-obtained viral suspensions showing the serotype of the B/HK/72 parent and the infectivity pattern of the Brigit strain parent in the AOS system is named R 75 (ATCC VR789).

Recombinant R 75 is submitted to two passages in SPF embryonated chicken eggs to obtain a substantial amount of R 75 recombinant.

In the following Table IV, the characteristics of the recombinant are summarized and compared to those of the Brigit and B/HK/5/72 parents.

TABLE IV

| Strain | Serotype Brigit | Serotype B/HK 5/72 | $EID_{50}/$ $(AOS)ID_{50}$ | Hemagglutinin thermosensitivity | 30° C sheep red blood cells hemagglutination |
|---|---|---|---|---|---|
| Brigit | + | − | + | + | unstable |
| B/HK/5/72 | − | + | − | − | stable |
| Recombinant R 75 | − | + | + | − | stable |

EXAMPLE 8

To one dosage unit ($10^{7.5}$ $EID_{50}$) of the freeze-dried influenza type B virus vaccine (R 22 strain,ATCC VR788) prepared as indicated in example 5, there is added one dosage unit ($10^{7.5}$ $EID_{50}$) of live attenuated type A influenza virus (Alice strain,ATCC VR776) in 0.5 ml. of a 5 % sucrose solution.

The so-obtained bivalent vaccine is administered as drops in the nostrils and the administration is repeated 14 day later. Seroconversion for both components (type B and type A) is observed 16 days after the second administration.

EXAMPLE 9

A sample of influenza type B virus strain B/HK/5/72 (ATCC VR791) the hemagglutinin of which is different from that of the Brigit strain, is inoculated in the allantoic cavity of 10 to 11 day-old embryonated chicken eggs (inoculum : 0.2 ml./egg), and submitted to three passages, in order to obtain a substantial amount of virus. At the end of the third passage, a viral suspension is obtained, the titer of which is $10^8 EID_{50}$/ml. Aliquots (0.2 ml.) of the undiluted suspension are inoculated in the allantoic cavity of SPF (specific pathogen free) embryonated eggs; after incubation for 2 hrs. at 33° C, aliquots (0.2 ml.) of a suspension of Brigit strain (obtained in example 1) having a titer of $10^{7.5} EID_{50}$/ml., are inoculated in the same eggs. The eggs are then incubated for 16 hrs. at 33° C and the allantoic fluids are harvested.

Aliquots (0.25 ml.) of anti-Brigit strain serotype rabbit serum previously heated for 1 hour at 56° C are mixed with aliquots (0.25 ml.) of the harvested allantoic fluid. The mixture is then maintained for 1 hour at 37° C. SPF embryonated eggs are inoculated with 0.2

EXAMPLE 10

The pooled allantoic fluids obtained in example 9 are sterility and safety tested, mixed with peptone as stabilizer in order to reach a final concentration of 5 % of peptone and distributed into 3 ml. glass vials in order to obtain a dosage unit (i.e. at least $10^7 EID_{50}$) of virus. The mixture is then freeze-dried and the vials sealed or tightly stoppered.

This passage level is used as a vaccine batch. For vaccine administration, the contents of one vial is reconstituted by adding 0.5 ml. of water or saline or a 5 % sucrose solution and administered as drops in the nostrils.

Clinical trials were performed in 24 volunteers. Each volunteer received with a 11 to 14 day interval two nasal administrations of the extemporaneously reconstituted vaccine, R 75 strain (ATCC VR789). At each administration, subjects were given a virus concentration of $10^{7.8} EID_{50}$ of the reconstituted vaccine in saline solution (5 drops in each nostrils).

The serological results are summarized in the following table V.

TABLE V

| Subject | Serum titer (HI) before vaccination | Serum titer (HI) after 2nd. vaccination |
|---|---|---|
| 1 | 256 | 256 |
| 2 | 16 | 32 |
| 3 | 16 | 32 |
| 5 | <4 | 32 |
| 9 | 16 | 32 |
| 13 | 8 | 32 |
| 23 | <4 | 16 |
| 25 | <4 | 64 |
| 27 | 16 | 64 |
| 28 | 4 | 32 |
| 29 | 16 | 64 |
| 30 | 4 | 32 |
| 32 | 16 | 64 |

TABLE V-continued

| Subject | Serum titer (HI) before vaccination | Serum titer (HI) after 2nd. vaccination |
|---|---|---|
| 35 | 8 | 128 |
| 36 | 8 | 32 |
| 37 | 128 | 128 |
| 40 | 8 | 16 |
| 43 | 64 | ≥ 256 |
| 47 | 4 | 16 |
| 49 | 16 | 32 |
| 59 | 64 | 64 |
| 63 | 4 | 64 |
| 65 | 4 | 64 |
| 66 | <4 | 16 |

Seroconversion (fourfold increase of HI titer) was observed in 75 % of the subject showing an prevaccinal HI titer 16.

EXAMPLE 11

Suspensions of the influenza type B R 75 strain (ATCC VR789) and of the influenza type A "Alice" strain (ATCC VR 776) are mixed, peptone is added as stabilizer in order to reach a final concentration of 5 % of peptone and the mixture is distributed into 3 ml. glass vials in order to contain at least $10^7 EID_{50}$ of each virus. The mixture is freeze-dried and the vials sealed or tightly stoppered. For vaccine administration, the contents of one vial is reconstituted by adding 0.5 ml. of water or saline or a 5 % sucrose solution and administered as drops in the nostrils.

We claim:

1. A live influenza virus vaccine effective on intranasal administration comprising an effective amount of an attenuated influenza type B virus recombinant strain obtained by recombining a first vaccinal attenuated influenza type B virus strain resistant to serum inhibitors with a second influenza type B virus strain, and isolating a recombinant having (1) at least one marker property of the said first virus strain selected from the group consisting of positive allantoic membrane on shell and resistance to serum inhibitors and (2) the antigenic characteristics of the said second virus strain, and a carrier therefor.

2. A live influenza virus vaccine according to claim 1, wherein the first vaccinal attenuated influenza type B virus strain resistant to serum inhibitors is influenza type B Brigit strain (ATCC VR 786).

3. A vaccine according to claim 2, wherein the second virus strain is influenza type B strain B/Hong Kong/5/72 (ATCC VR 791).

4. A vaccine according to claim 3, wherein the recombinant is influenza type B strain (ATCC VR 788).

5. A vaccine according to claim 3, wherein the recombinant is influenza type B strain (ATCC VR 789).

6. A vaccine according to claim 2, wherein the second virus strain is influenza type B strain B/Hong Kong/8/73 (ATCC VR 792).

7. A vaccine according to claim 6, wherein the recombinant is influenza type B strain (ATCC VR 787).

8. A live influenza virus vaccine effective on intranasal administration comprising a vaccine according to claim 1 and an effective amount of an attenuated influenza type A virus vaccine effective on intranasal administration.

9. A vaccine according to claim 8, wherein the attenuated influenza type A virus is influenza type A virus Alice strain (ATCC VR 776).

10. A vaccine according to claim 7, wherein the influenza type B strain recombinant is ATCC VR 789.

11. A vaccine according to claim 1, wherein the effective amount of the recombinant is at least $10^7 EID_{50}$.

12. A vaccine according to claim 1, in which peptone is present as stabilizer.

* * * * *